(12) United States Patent
Murphy

(10) Patent No.: US 10,413,394 B2
(45) Date of Patent: Sep. 17, 2019

(54) DEVICES AND METHODS FOR PREVENTING INCISIONAL HERNIAS

(71) Applicant: Prevent Patch, LLC, Bloomfield Hills, MI (US)

(72) Inventor: John W. Murphy, Bloomfield Hills, MI (US)

(73) Assignee: Prevent Patch, LLC, Bloomfield Hills, MI (US)

( * ) Notice: Subject to any disclaimer, the term of this patent is extended or adjusted under 35 U.S.C. 154(b) by 269 days.

(21) Appl. No.: 15/445,197

(22) Filed: Feb. 28, 2017

(65) Prior Publication Data

US 2017/0165045 A1 Jun. 15, 2017

Related U.S. Application Data

(63) Continuation of application No. 14/530,170, filed on Oct. 31, 2014, now Pat. No. 9,622,844.

(51) Int. Cl.
*A61F 2/00* (2006.01)
*A61B 17/04* (2006.01)
*A61B 17/00* (2006.01)

(52) U.S. Cl.
CPC ........ *A61F 2/0063* (2013.01); *A61B 17/0466* (2013.01); *A61F 2/0077* (2013.01); *A61B 2017/00004* (2013.01); *A61F 2002/0068* (2013.01); *A61F 2002/0081* (2013.01); *A61F 2210/0004* (2013.01); *A61F 2220/0083* (2013.01); *A61F 2250/0097* (2013.01)

(58) Field of Classification Search
CPC .................. A61F 2/0063; A61F 2/0077; A61F 2002/0081
See application file for complete search history.

(56) References Cited

U.S. PATENT DOCUMENTS

| | | | |
|---|---|---|---|
| 4,259,959 | A | 4/1981 | Walker |
| 4,854,316 | A | 8/1989 | Davis |
| 5,531,790 | A | 7/1996 | Frechet et al. |
| 6,485,503 | B2 | 11/2002 | Jacobs et al. |
| 6,712,838 | B2 | 3/2004 | D'Aversa et al. |
| 6,991,643 | B2 | 1/2006 | Saadat |
| 7,566,337 | B2 | 7/2009 | Sogaard-Andersen et al. |

(Continued)

FOREIGN PATENT DOCUMENTS

| | | |
|---|---|---|
| GB | 2430372 A | 3/2007 |
| WO | WO-2008/140439 A1 | 11/2008 |
| WO | WO-2014/048981 A1 | 4/2014 |

OTHER PUBLICATIONS

Cost analysis of the use of small stitches when closing midline abdominal incisions; published Jul. 10, 2013; Millbourn et al.; 5 pages.

(Continued)

*Primary Examiner* — Julian W Woo

(74) *Attorney, Agent, or Firm* — Butzel Long; Gunther J. Evanina

(57) ABSTRACT

A reinforcement device comprises a sheet of biocompatible material equipped with a plurality of hooks for reinforcing the closure of a surgical incision, including elongated abdominal incisions. The reinforcement device, when implanted through surgery, reduces the likelihood of and/or prevents incisional hernias. The reinforcement device may be included in a surgical kit.

16 Claims, 3 Drawing Sheets

(56) References Cited

U.S. PATENT DOCUMENTS

| | | | |
|---|---|---|---|
| 7,662,169 B2 | 2/2010 | Wittmann | |
| 8,357,172 B2 | 1/2013 | Harper | |
| 8,657,853 B2 | 2/2014 | Straehnz | |
| 8,679,153 B2 | 3/2014 | Dennis | |
| 8,759,287 B2 | 6/2014 | Robson | |
| 8,795,384 B2 | 8/2014 | Nelson et al. | |
| 9,622,844 B2* | 4/2017 | Murphy | A61F 2/0063 |
| 9,839,504 B2* | 12/2017 | Miller | A61F 2/0063 |
| 9,839,505 B2* | 12/2017 | Romuald | A61F 2/0063 |
| 10,052,184 B2* | 8/2018 | Deichmann | A61F 2/0063 |
| 10,076,395 B2* | 9/2018 | Meneghin | A61F 2/0063 |
| 2005/0043818 A1 | 2/2005 | Bellon Caneiro et al. | |
| 2006/0259075 A1 | 11/2006 | Mandelbaum | |
| 2009/0192532 A1 | 7/2009 | Spinnler et al. | |
| 2012/0232334 A1 | 9/2012 | Bell et al. | |
| 2018/0070949 A1* | 3/2018 | Karimov | A61B 17/12009 |

OTHER PUBLICATIONS

Small bitres versus large bites for closure of abdominal midline incisions (STITCH): a double-blind, multicentre, randomised controlled trial; published www.thelancet.com vol. 386, Sep. 26, 2015, 7 pages.

Effect of stitch length on wound complications after closure of midline incisions; accepted for publication Oct. 23, 2008; Millbourn et al.; 4 pages.

* cited by examiner

DEVICES AND METHODS FOR PREVENTING INCISIONAL HERNIAS

CROSS-REFERENCE TO RELATED APPLICATIONS

This application is a continuation of U.S. application Ser. No. 14/530,170, filed Oct. 31, 2014 (now U.S. Pat. No. 9,622,844), which is incorporated herein by reference in its entirety.

TECHNICAL FIELD

This disclosure relates to medical devices, kits, and methods for reinforcing incision closures. Such devices, kits and methods may reduce the likelihood of incisional hernias.

BACKGROUND

Incisional hernias are detectable defects in a surgical site following the creation of a surgical incision. Such hernias may become apparent as a palpable defect; that is, abdominal contents may protrude beyond where they should and therefore can be physical felt. In some instances, incisional hernias may present merely as a protrusion within a healed incision.

Incisional hernias following surgery are a common complication following certain surgeries, including but not limited to a laparotomy. A laparotomy is a surgical procedure involving a incision through the abdominal wall to gain access into the abdominal cavity. There are numerous reasons why a particular patient might suffer from an incisional hernia following a laparotomy or other surgery. Patients suffering from obesity, diabetes, or malnutrition may be more susceptible to an incisional hernia. A patient may have poor tissue, or an infection at the incision site, making him or her more susceptible. In other instances, a closure of an incision may not be sufficiently strong to guard against incisional hernias. An unfortunate result is that incisional hernias are not particularly rare. In fact, following a laparotomy, the incidence of incisional hernia has ranged from 15-40%.

The incidence of incisional hernias is serious. Correction usually calls for surgical intervention, re-operation, and/or prolonged hospitalization. Incisional hernias also may increase morbidity and mortality. In other words, the costs to the health care system and the patient are significant, fiscally and otherwise.

It is desireable to reduce the incidence of incisional hernias, or to prevent them during an initial operation, by reinforcing surgical closures using medical devices, kits and/or methods.

DETAILED DESCRIPTION

Multiple embodiments of the disclosed devices, kits and methods are described with reference to only a few exemplary drawings. Although a particular embodiment may be illustrated and described herein as including particular components in a particular configuration, such components and configuration are for exemplary purposes only. The figures and descriptions of the embodiments described herein are not intended to limit the breadth or the scope of the inventive concepts or the appended claims. Rather, the figures and detailed descriptions are provided to illustrate the inventive concepts to a person of ordinary skill in the art and to enable such person to make and use the inventive concepts.

Figure 1:
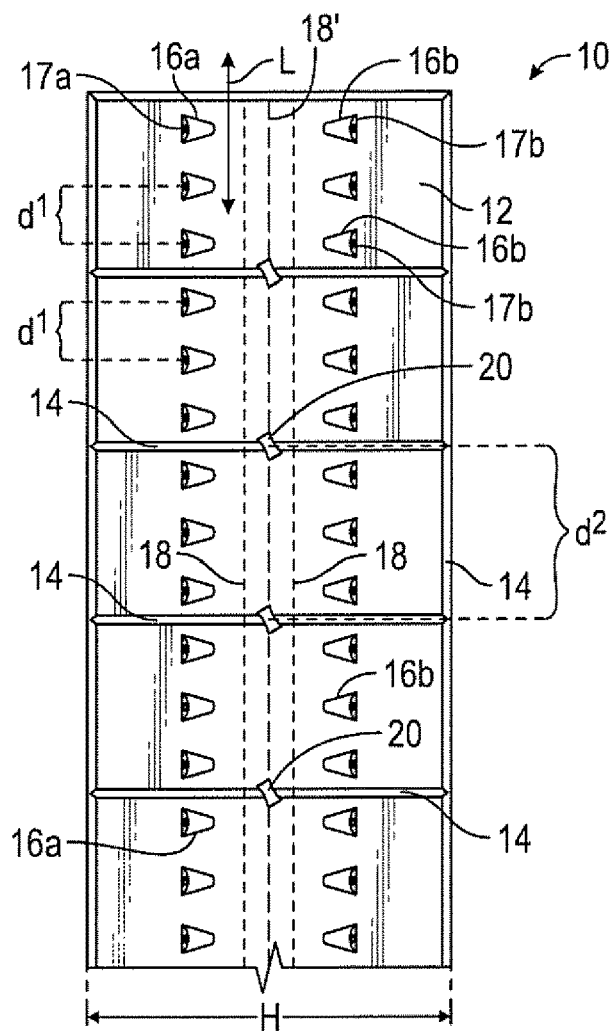
FIG. 1 is a top view an exemplary reinforcement device.
Figure 2:
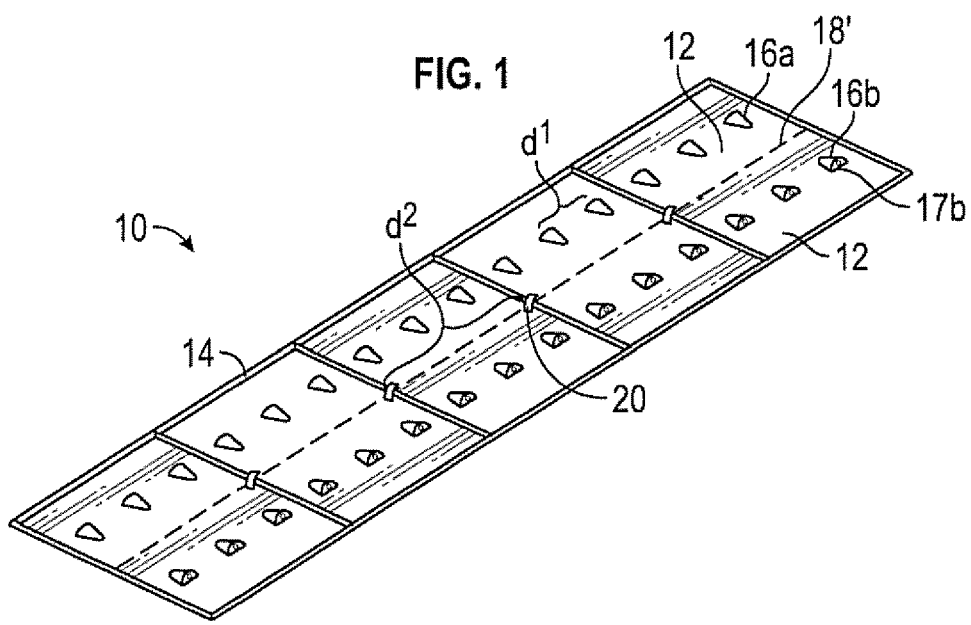
FIG. 2 is perspective view of an exemplary reinforcement device.

With reference to FIGS. 1-2, exemplary reinforcement device 10 is shown. Reinforcement device 10 comprises a sheet of biocompatible material which is exemplified as mesh sheet 12. The biocompatible material may be bioabsorbable, non-bioabsorbable, partially bioabsorbable, or some combination of one or more of these. The biocompatible material may comprise any of a number of materials. By way of non-limiting examples, bioabsorbable materials may comprise polyhydroxy acids, polylactides, polyglycolides, polyhydroybutyrates, polyhydroxyvaleriates, polycaprolactones, polydioxanones, synthetic and natural oligo- and polyaminoacids, polyphosphazenes, polyanhydrides, polyorthoesters, polyphosphates, polyphosphonates, polyalcohols, polysaccharides, and polyethers. By way of non-limiting examples, non-bioabsorbable materials may comprise polyalkenes, polyethylene, fluorinated polyolefins, polytetrafluoroethylene, polyvinylidenefluoride, polyamides, polyurethanes, polyisoprenes, polystryrenes, polysilicones, polycarbonates, polyaryletherketones, polymetacrylates, polyacrylates, aromatic polyesters, and polyimides.

Mesh sheet 12 may comprise a single layer of material, or it may comprise two or more layers of material. Separate layers of material may or may not be co-extensive in length and/or width. Mesh sheet 12 may be at least partially woven or knitted. Mesh sheet 12 have a reinforcing material 14 in or on at least a portion of the mesh sheet 12. Reinforcing material may comprise any of a number of biocompatible materials, including but not limited to synthetic composite materials such as polyglactin and/or poly p-dioxane undyed yarn. The reinforcing material can be applied to the mesh sheet 12 using any of a number of impregnating or application techniques. Reinforcing material 14 may be in the form of ribs or strips on at least a portion of the periphery of mesh sheet 12. Reinforcing material 14 may also be applied in the horizontal direction as a plurality of spaced apart rows. Although the strips of reinforcing material depicted in the drawings run the entire periphery of the reinforcing device 10 and include a plurality of spaced apart rows at a common length distance between adjacent rows, other configurations are contemplated.

Mesh sheet 12 also is equipped with two or more columns of hooks 16a, 16b that run parallel or substantially parallel to a longitudinal axis L of reinforcement device 10. The hooks depicted are shaped like inverted U's, which are similar to wickets used in croquet. Other shapes and configurations of hooks are contemplated; the hooks are structures though which suture may pass in sewing the reinforcement device 10 to the patient. These hooks 16a, 16b may be integrally formed with the mesh sheet 12 or added on or to the mesh sheet 12 using any of a number of methods. In the depicted embodiment, the common longitudinal distance between hooks within a spaced apart column is d1.

One or more of hooks 16a, 16b may also be affiliated with an aperture 17a, 17b. In the depicted embodiment, each of hooks 16a, 16b is affiliated with an aperture 17a, 17b. The apertures 17a, 17b are sized and shaped so that a marking end of a marking device may mark a patient's fascia where a needle and suture are to pierce a patient's fascia to attach the reinforcement device 10 to the patient. The ability to mark fascia may provide guidance in the form of a template to a surgeon for precision of location in a suturing process. Placement of apertures 17a and 17b is sufficiently distant from an incision point to avoid wound dehiscence.

In the depicted embodiment of FIGS. 1 and 2, the column with hooks 16a and the column with hooks 16b are on opposite sides of a longitudinal center region 18 that is substantially rectangular and encompasses center line 18'. Center region 18 falls between the spaced apart columns of hooks. Center region 18 extends from opposite ends of the mesh sheet 12, top edge to bottom edge. The top edge and bottom edge are opposite each other and are perpendicular to or substantially perpendicular to the longitudinal axis of mesh sheet 12. Within this center region 18, there is a reinforcing column of hooks 20. Hooks 20 may be of the same or a different material and/or configuration than the hooks 16a, 16b. Hooks 20 may be supported by reinforcing material 14. The longitudinal distance between hooks 20 is d2. In the depicted embodiment, d2 is greater than d1. Different configurations and variations between the length d1 and d2 are contemplated. For example, d2 may be 1.5× greater, 2× greater, 2.5× greater, 3× greater, 3.5× greater or 4× greater than d1. Different ratios may also be suitable.

Generally, reinforcement devices 10 may have a number of shapes and dimensions. In one non-limiting exemplary embodiment of a rectangular reinforcement device 10, a horizontal width of mesh sheet 12 is about 5 cm, a longitudinal length is about 15 cm or about 30 cm, d1 is about 1 cm, and d2 is about 3 cm. The length of reinforcement device 10 depends upon the length of incision, and a surgeon may cut a commercially available reinforcement device 10 to fit the size of a particular incision. The about 5 cm width overlap of the incision may add tensile strength to the wound to assist in reducing the incidence of incisional hernias. Generally, for about every 1 cm of d1 required to close a particular incision, about 4 cm of suture may be used. Stated another way, an exemplary ratio of suture length to wound length of 4 is one embodiment suited for prevention or reduction of incidence of incisional hernias. Different dimensions and different ratios are contemplated; those identified in this paragraph are merely exemplary teachings.

Figure 3:
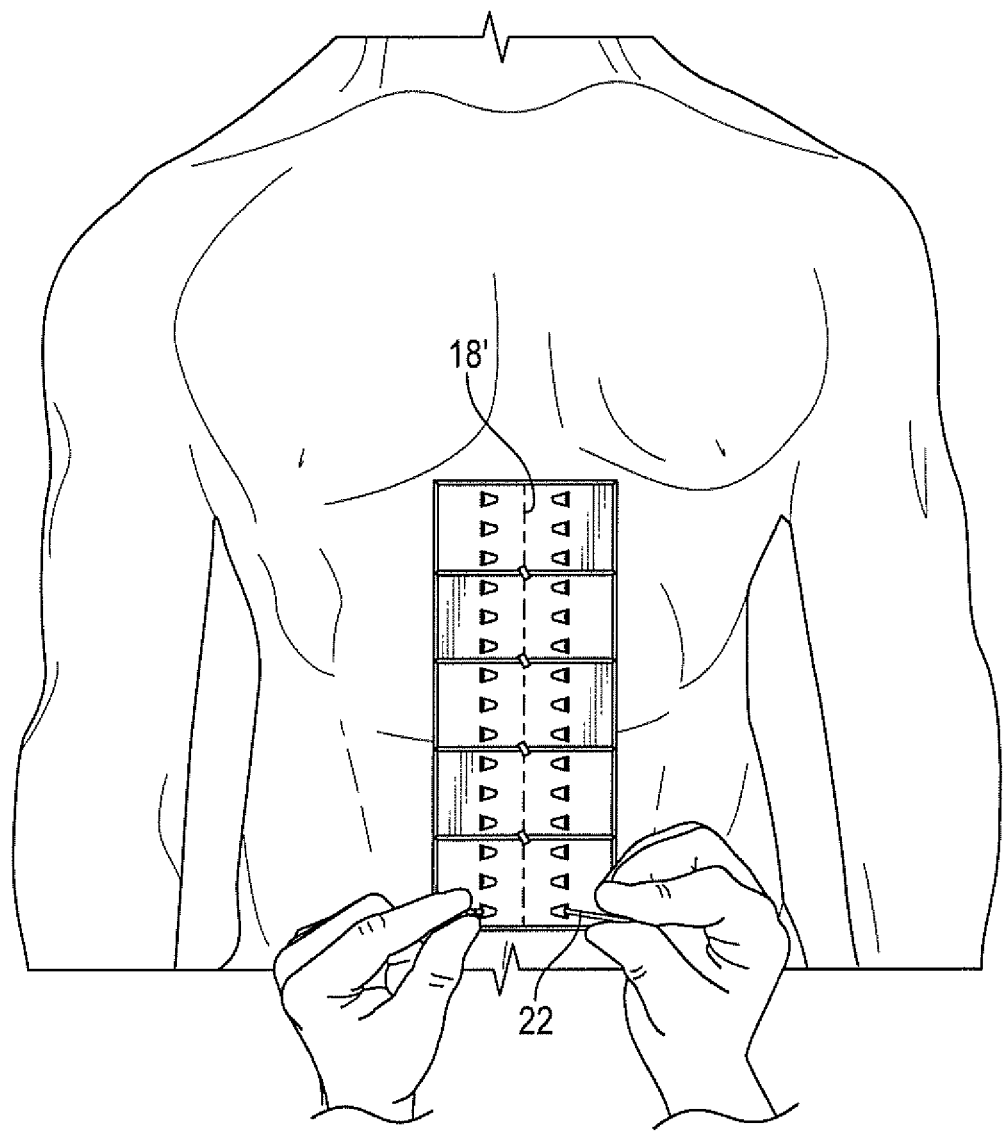
FIG. 3 is a top view of an exemplary reinforcement device in connection with an abdomen of a patient.
Figure 4:
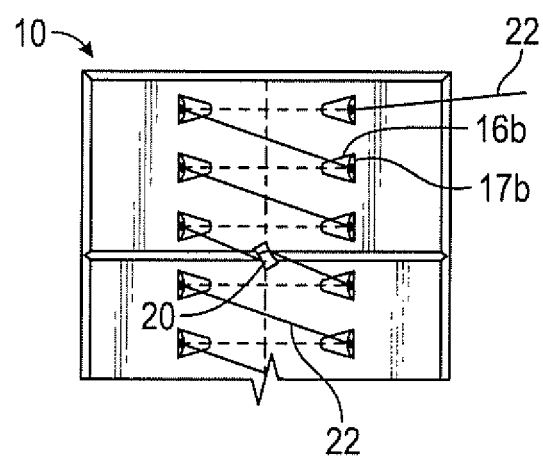
FIG. 4 is a perspective view of suture connecting an exemplary reinforcement device to a patient through a plurality of hooks.
Figure 5:
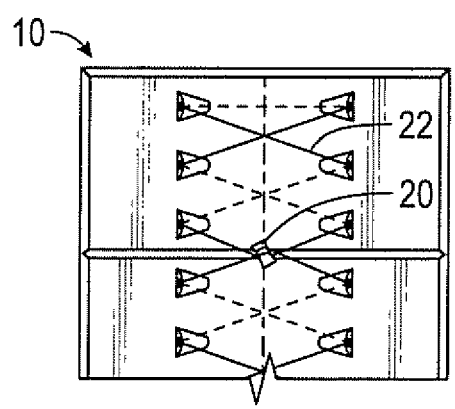
FIG. 5 is a perspective view of suture connecting an exemplary reinforcement device to a patient through a plurality of hooks.

Referring to FIGS. 3-5, examples are shown where a reinforcement device 10 is used in connection with the closing of an abdominal incision. The surgeon places the reinforcement device 10 over the fascia, attempting to align the center region 18, and the center line 18' with the incision itself. The surgeon may then mark a patient's fascia through the apertures 17a and 17b to indicate where the needle and suture are to pierce fascia to sew the reinforcement device 10 to the patient. In one non-limiting embodiment, the apertures 17a and 17b are about 1 cm in horizontal distance from the center line 18'.

The particular suture 22 and/or needle(s) (not shown) for use with the reinforcement device 10 may be provided in a surgical kit including the reinforcement device 10, along with other medicaments, sterilizers, marking devices, cutting tools, and other medical devices and equipment. Any of a number of commercially available sutures 22 may be used with the reinforcement device 10. The suture 22 may, for example, be bioabsorbable or non-bioabsorbable.

When the fascia is marked, a surgeon may position reinforcement device 10 in a position to commence suturing. Such position may be intra-peritoneal or extra-peritoneal, depending upon the materials of the reinforcement device 10. For example, non-bioabsorbable materials may be positioned to avoid potential for adhesion to internal organs. Generally, the suturing involves inserting the sutures 22 through the fascia, then looping the suture through hooks 16a to fascia to 16b to fascia to 16a to fascia to 16b, etc. in a series of generally Z-shaped formations or a series of generally X-shaped formations, possibly using a double needled suturing technique. Eventually, as a suturing pattern encounters a hook 20 in its general path, the surgeon may gain additional reinforcement by passing the suture 22 at least once through and/or around hook 20 before completing the connection between a hook 16a and a hook 16b. An exemplary non-limiting suturing pattern is indicated in FIG. 4, and another in FIG. 5. Other suturing patterns are contemplated.

With regard to the devices, kits, methods, etc. described herein, it should be understood that, although the steps of such methods, etc. have been described as occurring according to a certain ordered sequence, such methods could be practiced in an order other than the order described. It should also be understood that certain steps could be performed simultaneously, that other steps could be added, or that certain steps could be omitted.

The above description is intended to be illustrative, not restrictive. The scope of the invention should be determined with reference to the appended claims along with the full scope of equivalents. It is anticipated and intended that future developments will occur in the art, and that the disclosed devices, kits and methods will be incorporated into such future embodiments. Thus, the invention is capable of modification and variation and is limited only by the following claims.

What is claimed as new and desired to be protected by Letters Patent of the United States is:

1. A device for reinforcing closures of abdominal surgery, comprising:
    a mesh sheet of biocompatible material having a longitudinal axis and a horizontal axis; said mesh sheet having a first side and an opposed second side;
    a plurality of spaced apart columns of hooks on the first side of the mesh sheet running substantially parallel to one another and substantially parallel with the longitudinal axis; the hooks in each column having a common longitudinal distance between each adjacent hook; and
    a reinforcing column of hooks on said first side of the sheet between the spaced apart columns of hooks, wherein the hooks in the reinforcing column have a greater common longitudinal distance between hooks than in the spaced apart columns of hooks, the hooks in all columns being configured to receive a suture and being spaced relative to one another such that, for attachment of the device to a body of a patient, the spacing between hooks is dimensioned for a ratio of a length of suture to a length of an incision in the body of the patient of about 4:1; wherein each of the hooks is positioned near an affiliated aperture in said mesh sheet.

2. The device of claim 1 wherein the mesh sheet comprises bioabsorbable material.

3. The device of claim 1 wherein the mesh sheet comprises non-bioabsorbable material.

4. The device of claim 1 wherein the mesh sheet is a single layer contiguous sheet.

5. The device of claim 1 wherein the mesh sheet comprises at least two layers.

6. The device of claim 1 wherein the plurality of spaced apart columns comprises a first column on a first side of a center region and the second column on a second side of the center region, wherein the center region is an elongated substantially rectangular area that extends from a first edge of the sheet to a second edge of the sheet, the first and second edges being opposite one another and being substantially perpendicular to the longitudinal axis of the sheet.

7. The device of claim 1 wherein the sheet comprises a reinforcing material on at least a portion of its periphery.

8. The device of claim 7 wherein reinforcing material is also provided in spaced apart rows substantially parallel to the horizontal axis.

9. The device of claim 1 wherein the hooks in the spaced apart columns are shaped substantially like an inverted U.

10. The device of claim 1 wherein the hooks in the reinforcing column are shaped substantially like an inverted U.

11. The device of claim 1 wherein each aperture is sized large enough for a marking end of a marking device to penetrate.

12. A surgical kit, comprising:
the device of claim 1; and
suture.

13. The surgical kit of claim 12 wherein the suture is bioabsorbable.

14. The surgical kit of claim 12 wherein the suture is non-bioabsorbable.

15. A device for reinforcing closures of abdominal surgical incisions, comprising:

a mesh sheet having a longitudinal axis and a horizontal axis; said mesh sheet having a first side and an opposed second side;

a plurality of spaced apart columns of hooks on the first side of the mesh sheet running substantially parallel to one another and substantially parallel with the longitudinal axis, the hooks in each column having a common longitudinal distance between each adjacent hook, each hook in the spaced apart columns having an affiliated aperture adapted for use in marking of tissue for placement of sutures;

a reinforcing column of hooks on the first side of the sheet between the spaced apart columns of hooks, wherein the hooks in the reinforcing column have a greater common longitudinal distance between hooks than in the spaced apart columns of hooks; and a center region that is an elongated substantially rectangular area that extends from a first edge of the sheet to a second edge of the sheet, the first and second edges being opposite one another and being substantially perpendicular to the longitudinal axis of the sheet, such that the plurality of spaced apart columns comprises a first column on a first side of the center region and a second column on a second side of the center region, the hooks in all columns being configured to receive a suture and being spaced relative to one another such that, for attachment of the device to a body of a patient, the spacing between hooks is dimensioned for a ratio of a length of suture to a length of an incision in the body of the patient of about 4:1, wherein each of the hooks is positioned near an affiliated aperture in said mesh sheet.

16. The device of claim 15, wherein the mesh sheet comprises a strip of reinforcing material about at least a portion of its periphery.

* * * * *